United States Patent [19]

Zweymüller et al.

[11] Patent Number: 5,443,520
[45] Date of Patent: Aug. 22, 1995

[54] CEMENTLESS FIXATION ELEMENT FOR AN ARTIFICIAL HIP JOINT WITH ROTATING COVER ELEMENT

[75] Inventors: K. Zweymüller, Vienna, Austria; André Deckner, Paris, France

[73] Assignee: Plus Endoprothetik AG, Switzerland

[21] Appl. No.: 166,388

[22] Filed: Dec. 7, 1993

[30] Foreign Application Priority Data

Dec. 7, 1992 [EP] European Pat. Off. ........... 92120836

[51] Int. Cl.6 ............................ A61F 2/32; A61F 2/34
[52] U.S. Cl. ........................................ 623/22; 623/18; 623/23
[58] Field of Search ............................ 623/22, 23, 18

[56] References Cited

U.S. PATENT DOCUMENTS

| | | | |
|---|---|---|---|
| 4,662,891 | 5/1987 | Noiles | 623/22 |
| 4,919,676 | 4/1990 | Zweymuller et al. | 623/22 |
| 5,009,666 | 4/1991 | Van Syckle et al. | 623/23 |
| 5,074,881 | 12/1991 | Thull et al. | 623/22 |

FOREIGN PATENT DOCUMENTS 2676172  5/1991  France .

Primary Examiner—David Isabella
Assistant Examiner—Laura Fossum
Attorney, Agent, or Firm—Andrus, Sceales, Starke & Sawall

[57] ABSTRACT

A metal fixation element is disclosed for receiving a plastic socket component of an artificial hip joint. The fixation element includes a frontal region which faces the pelvic bone. The frontal region has a central bore, with a screw thread to receive an insertion tool. The element also includes at least one conically tapering wall spaced from the frontal region. A self-tapping screw thread on the outer surface of the tapering wall provides for cementless fixation of the element in the pelvic bone. There is further provided an additional conically tapering wall between the frontal region and the first conically tapering wall. Three apertures are located in the frontal region. A cover element is rotatably mounted within the fixation element closely abutting the frontal region. The cover element has three equally spaced openings separated by continuous positions for selective opening and closing of the three apertures in the frontal region.

15 Claims, 2 Drawing Sheets

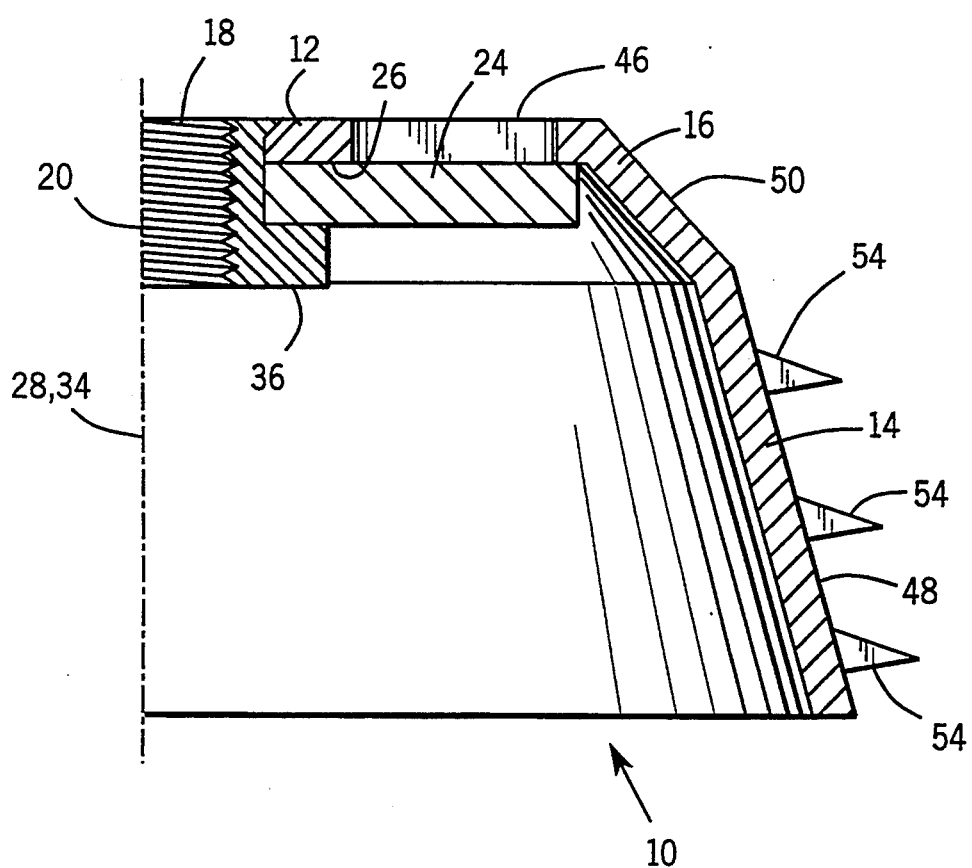

CEMENTLESS FIXATION ELEMENT FOR AN ARTIFICIAL HIP JOINT WITH ROTATING COVER ELEMENT

FIELD OF THE INVENTION

The present invention relates to a fixation element for receiving a socket component of an artificial hip joint for cementless anchoring in a pelvic bone. Typically such an element is made of metal and is adapted to receive a plastics socket component.

DESCRIPTION OF THE PRIOR ART

A fixation element of this kind is described in European Patent EP-B1-0 296 274. Here the fixation element comprises a frontal region for directly facing the pelvic bone and a conically tapering wall adjoining the frontal region. In the frontal region a central, threaded bore is provided to receive a tool for insertion of the fixation element during a hip replacement operation. Because the long axis of the insertion tool to be screwed into the threaded bore coincides with the longitudinal axis or axis of rotation of this fixation element, positioning of this fixation element by changing the axial direction of the insertion tool is considerably facilitated. In addition this fixation element has at least one aperture in the frontal region through which spongiosa tissue, especially autologous or homologous bone material, can be placed and packed at the "floor" of the cavity in the pelvic bone. The cavity is surgically created to receive the artificial hip-joint socket, so that the space behind this fixation element can be filled in. Finally, this fixation element is also provided with a self-tapping screw thread located on the outer surface of the conically tapering wall adjacent to the frontal region. In this way the fixation element can be very simply and accurately positioned in the pelvic bone and simultaneously anchored there.

This fixation element for cementless fixation of an artificial hip-joint socket in the pelvic bone is extremely stable and highly resistant to any kind of socket migration, so that with this fixation element a long service life following surgery is achieved. However, although this fixation element has definitely proved its value in practice, it has been found not always to make adequate contact with the pelvic bone, especially in the frontal region and particularly when the pelvic bone is relatively hard. Furthermore, when this fixation element is inserted into the cavity previously created in the pelvic bone, it has a tendency to tilt, which complicates the surgical procedure or can even result in inaccurate positioning. Finally, a deformation of the frontal region due to the apertures within it has often been observed during insertion of this fixation element into the previously created cavity in the pelvic bone.

SUMMARY OF THE INVENTION

The object of the present invention is to overcome or substantially mitigate the aforementioned disadvantages and to provide a fixation element of this generic kind that gives a relatively large area of contact with the bone, especially in the frontal region, mitigates tilting when inserted into a previously created cavity, and substantially prevents deformation of the frontal region as a consequence of the large forces exerted on the fixation element when it is screwed in.

According to the present invention there is provided a fixation element for receiving a socket component of an artificial hip joint comprising a frontal region for facing a pelvic bone and defining a screw-threaded central bore to receive an insertion tool. The frontal region includes at least one aperture therein. The fixation element includes a first conically tapering wall located adjacent said frontal region and having a self-tapping screw thread on its outer surface for cementless fixation of the element in the pelvic bone. The fixation element also includes a second conically tapering wall disposed between said frontal region and said first conically tapering wall.

Owing to this configuration in which a second conically tapering wall is present between the frontal region and the first conically tapering wall of the fixation element, a large contact area of the fixation element with the acetabular surface of the pelvic bone is achieved, even when the bone is very hard. A major consequence of such a double-conical structure, i.e. of the presence of two conically tapering walls, is a large-area bone contact in the frontal region of the fixation element. Furthermore, the configuration of the fixation element in accordance with the invention is especially advantageous with respect to surgical technique, inasmuch as tilting of the fixation element when it is inserted or screwed into the previously created cavity in the pelvic bones is reliably avoided owing to an improved self-centering of the implant. The frontal region is also made more resistant to bending by the additional conically tapering wall. Moreover, the shape of the fixation element as a result of the double-cone configuration is matched anatomically to the spherical shape of the acetabulum. This is particularly advantageous with respect to both increased stability against tilting and high initial tension in the bony cavity containing the socket, which results in rapid osteointegration of the implant and improved protection against migration due to tilting movements and other resistances. Quite apart from these advantages, with such a double-cone configuration of the fixation element in accordance with the invention, very little bone resection is necessary in the region of the "floor" of the socket cavity.

Preferably, said second conically tapering wall defines a conical angle $\alpha$ which is larger than a conical angle $\beta$ defined by the first conically tapering wall.

Preferably also, the second conically tapering wall defines a conical angle $\alpha$ which is in the range 30° to 60° inclusive.

The relative values and disposition of the angles $\alpha$ and $\beta$ enables a large-area contact of the fixation element with the bone material to be achieved along with a reliable avoidance of tilting of the fixation element and deformation of its frontal region.

Preferably also, a means is provided to close the aperture or apertures defined by the frontal region.

The aperture or apertures provide the operator with an opportunity for continuous visual control during the implantation. On the one hand, it is possible to observe whether the fixation element is being inserted or screwed in parallel to the "floor" of the cavity previously created in the pelvic bone. On the other hand, the depth of insertion and the moment when the frontal region of the fixation element comes into contact with the "floor" of the cavity previously created in the pelvic bone can be determined precisely. With this information, the operator can be certain of the correct time to stop pushing or screwing the fixation element into the cavity, and there is also less likelihood that the self-tapping thread on the outer surface of the fixation element will tear loose. The aperture in the frontal region of the fixation element according to the invention in addition considerably facilitates any spongiosa reconstruction that may be necessary after the fixation element has been inserted or screwed into the cavity provided for it in the pelvic bone. That is, pulverized bone or chips or particles of bone or the equivalent that have been inserted through the one or several apertures in the frontal region of the fixation element according to the invention are effectively prevented from falling back out by, for example, gradually closing the aperture. Therefore the connection of the fixation element to the socket component cannot be impaired by bone particles or the equivalent that fall back and are lodged between fixation element and socket component. Finally, The aperture in the frontal region of the fixation element prevents the bone from coming into contact with the plastic socket component that is to be inserted. As a result, the healing process is accelerated and long-term damage to the bone surrounding the fixation element is avoided.

Preferably also, a cover element is rotatably secured within the fixation element in opposed relation to an inner surface of said frontal region. The cover element is rotated about an axis perpendicular to said frontal region to open and close the aperture.

Preferably also, said frontal region defines three apertures which are of substantially equal size and which are uniformly spaced about a circumference defined by said frontal region. This gives good accessibility as well as high resistance to deformation. Further with this arrangement the forces transferred to the frontal region by way of the central threaded bore to receive the insertion tool, while the fixation element is being inserted or screwed into the cavity provided for it in the pelvic bone, are further transmitted to the two approximately conically tapering walls and on to the self-tapping thread in equal portions, by way of the three substantially identically formed connecting pieces or the equivalent. This feature tends to prevent deformation of the frontal region of the fixation element.

In this regard, preferably each of the three apertures extends over a substantially 60° segment or portion of said frontal region.

In a further development of the invention, preferably the cover element is substantially disk-shaped and defines three openings which are of substantially equal size and are uniformly spaced about the circumference of said cover element. Preferably also, each of three regions of said cover element located between said three openings extend over a substantially 60° segment or portion of said cover element. With this particular configuration of the cover element, the three apertures in the frontal region of the fixation element can be completely opened and completely closed.

Preferably also, the fixation element has a longitudinal axis of rotation which coincides with the axis of rotation of said cover element. This considerably simplifies construction of the fixation element.

Preferably also, a rivet rotatably attaches said cover element to said frontal region, said rivet defining a screw-threaded bore. This further simplifies the construction of the fixation element.

Preferably also, said cover element is attached to said frontal region with no tolerance and under compression. This prevents the cover element from opening of its own accord in the eventuality, which cannot be entirely ruled out, that there should later be relative movement or friction between the cover element on one hand and the socket component on the other.

Preferably also, an inner surface of the first conically tapering wall defines at least one circumferential groove which can engage a correspondingly arranged projection on an outer surface of the socket component. Thus, a catch or snap device or the equivalent is provided in order that the socket component can be anchored securely in the fixation element after the latter has been inserted or screwed into the cavity provided for it in the pelvic bone.

Preferably also, the frontal region, the first conically tapering wall and the second conically tapering wall are roughened on at least their outer surfaces with a mean roughness, according to a Gaussian distribution, of 5 $\mu$m. This feature particularly facilitates biological fixation by osteointegration.

Preferably also, the self-tapping screw thread comprises a plurality of teeth, the size, thickness and height of which are adapted to the size of said socket component for use therewith. In addition, preferably the self-tapping screw thread comprises a plurality of teeth, the shape of which is adapted to the qualities of hardness and porosity of said pelvic bone into which the element is to be fixed. Accordingly, in both the primary implantation and subsequent revision procedures the operator, during the surgery itself, can select a fixation element matched to the quality of the bone material in the pelvic region. The special form of the teeth, especially in the case of very hard bone material, contributes to a considerable enlargement of the contact surface between bone and implant, in that fixation is not brought about exclusively by the tips of the teeth inserted into the surrounding bone material. From this construction, a the further advantage results in that there are no points of peak tension, which usually can cause bone resorption and thus delay healing or even prevent correct healing. Moreover, the high cutting efficiency of the self-tapping thread, resulting from the geometry of the individual teeth, not only reduces the torque induced while inserting or screwing in the fixation element but also improves the overall quality of the implantation.

Further characteristics, advantages and details of the invention will become apparent in the following description of a preferred embodiment of the invention with reference to the accompanying drawings.

BRIEF DESCRIPTION OF THE DRAWINGS

FIG. 5 is a median half-section through the fixation element.

DESCRIPTION OF A PREFERRED EMBODIMENT

A fixation element 10, as shown in FIGS. 1 to 5, is intended to receive a socket component (not shown) of an artificial hip joint for cementless fixation of same in a pelvic bone. The socket component is intended to engage a ball component (not shown) of a femoral prosthesis. The fixation element 10 is made of metal or equivalent material, for example of titanium or a titanium alloy. The socket component itself, in contrast, is of plastics or an equivalent material, e.g. polyethylene.

The fixation element 10 comprises a frontal region 12 that is intended to face the pelvic bone, a conically tapering wall 14 adjacent to the frontal region 12, and an additional conically tapering wall 16 situated between the frontal region 12 and the first conically tapering wall 14.

Figure 4:
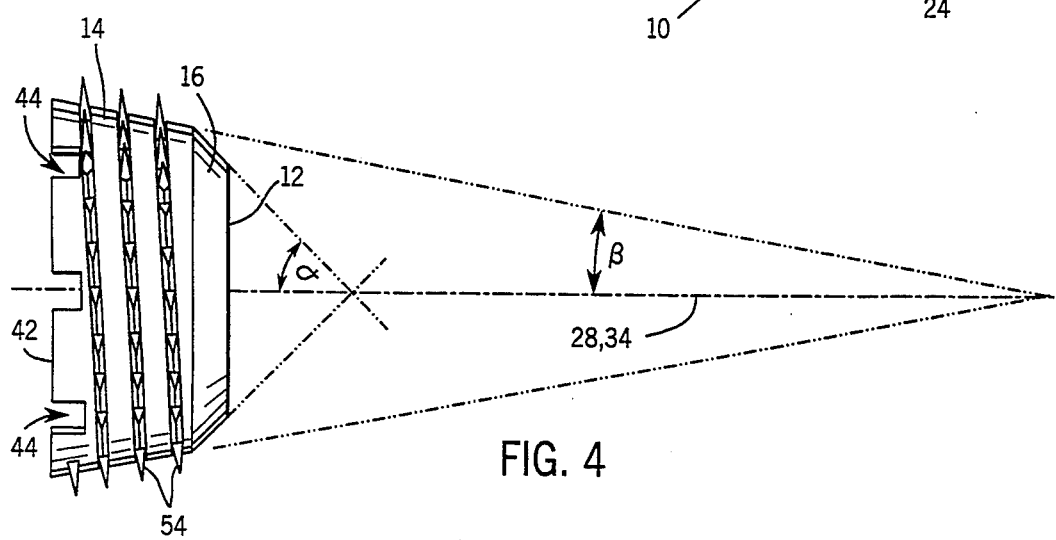
FIG. 4 is a side elevation of the fixation element.

As shown in FIG. 4, the conical angle $\alpha$ of the additional conically tapering wall 16 is larger than the conical angle $\beta$ of the first conically tapering wall 14. The conical angle $\alpha$ of the additional conically tapering wall 16 is in the range 30° to 60° inclusive and preferably about 45°. In comparison, the conical angle $\beta$ of the first conically tapering wall 14 is in the range 5° to 20° inclusive and preferably about 10°.

The frontal region 12 defines a central bore 18 with a screw thread 20 to receive an insertion tool (not shown).

Furthermore, in the frontal region 12 at least one aperture 22 is provided, which can be closed by a cover element 24 or equivalent. The cover element 24 is apposed to the inner surface 26 of the frontal region 12 and can be rotated about an axis 28 perpendicular to the frontal region 12.

Figure 1:
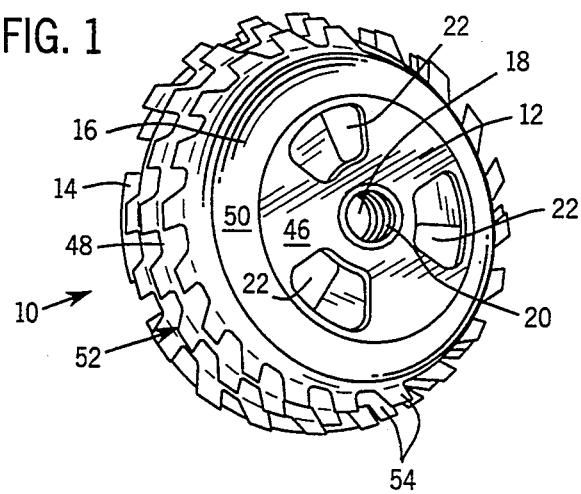
FIG. 1 is a perspective view from above of a fixation element according to the present invention.
Figure 2:
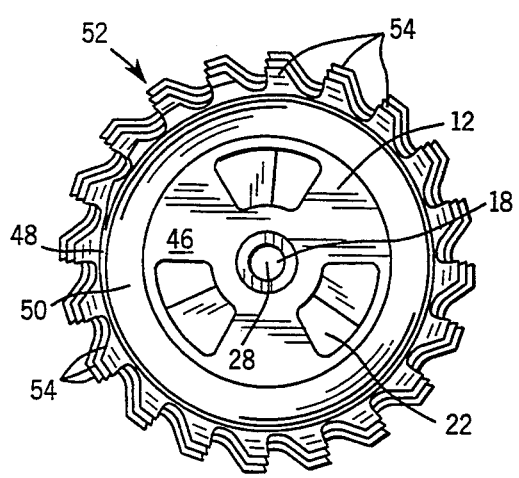
FIG. 2 is a plan view of the fixation element shown in FIG. 1.

In the illustrated embodiment of the fixation element shown in FIGS. 1 to 5, three apertures 22 of about equal size are provided, uniformly spaced about the circumference of the frontal region 12. As is shown in FIG. 2, each of the three apertures 22 extends over an approximately 60° segment of the frontal region.

The cover element 24 in this embodiment of the fixation element 10 is substantially disk-shaped and within it are three openings 30 of about equal size, spaced uniformly about the circumference of the cover element 24. The regions 32 of the cover element 24 between the openings 30 each also extend over an approximately 60° segment of the disk. With this arrangement, all three apertures 22 in the frontal region 12 can simultaneously be partially or completely closed by rotation of the cover element 24 so that the apertures 22 are covered by the regions 32 between the openings 30 of the cover element 24.

The axis of rotation 28 of the cover element 24 as shown in FIGS. 1 to 5 coincides with the longitudinal axis or axis of rotation 34 of the fixation element 10. To achieve an especially simple, unelaborate construction, the cover element 24 is rotatably attached to the frontal region 12 of the fixation element 10 by a rivet 36 or the equivalent, which includes the bore 18 with the screw thread 20. It is an advantage for the cover element 24 to be rotatably attached to the frontal region 12 with no tolerance and in particular under compression.

Figure 3:
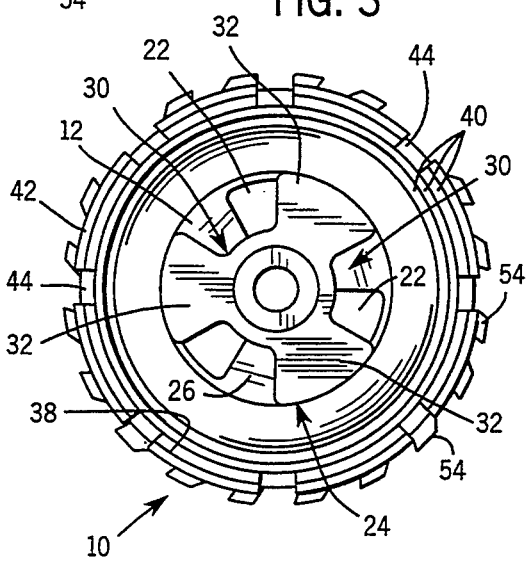
FIG. 3 is a view from below of the fixation element shown in FIGS. 1 and 2.

The fixation element 10 in accordance with the invention is connected to a socket component (not shown) by means of a catch or snap device or the equivalent. For this purpose in particular, at least one circumferential groove 40 or the equivalent is provided on the inner surface 38 of the first conically tapering wall 14 in order to engage correspondingly positioned projections on the outer surface of the socket component. The inner surface 38 of the first conically tapering wall 14 shown in FIG. 3 is provided with a total of three such circumferential grooves 40.

At the exposed edge 42 of the first conically tapering wall 14 there are further uniformly disposed a plurality of recesses 44 to engage with an insertion tool when the fixation element 10 is inserted or screwed into a prepared cavity in a pelvic bone during the surgical procedure, with the effect of enhancing force transmission. In addition, the recesses 44 cooperate with corresponding, peg-like projections on the socket component to simultaneously stabilize the socket component against rotational displacement.

Furthermore, the frontal region 12 and the two conically tapering walls 14, 16 are toughened at least on their outer surfaces 46, 48, 50, for example by sand blasting or the equivalent. In particular, the outer surface 46 of the frontal region 12, the outer surface 48 of the first conically tapering wall 14 and the outer surface 50 of the additional conically tapering wall 16 have a mean Gaussian distribution surface roughness of 5 $\mu$m.

As shown in FIGS. 1 to 5, a self-tapping screw thread 52 is disposed on the outer surface 48 of the first conically tapering wall 14. The self-tapping thread 52 is composed of a plurality of individual sawtooth-shaped cutting teeth 54 arranged one behind another. The size, thickness and height of the teeth 54 are adapted to the size of the socket component to be used. Furthermore, the shape or geometric configuration of the teeth 54 can be altered in various ways to correspond to the quality of any particular pelvic bone depending on whether the bone material is hard and sclerotic or soft and porous.

What is claimed is:

1. A fixation element for receiving a socket component of an artificial hip joint, comprising:
    a frontal region for facing a pelvic bone and having a screw-threaded central bore to receive an insertion tool and said frontal region having at least one aperture therein;
    a first conically tapering wall located adjacent said frontal region and having an outer surface including a self-tapping screw thread for cementless fixation of the element in the pelvic bone;
    a second conically tapering wall disposed between said frontal region and said first conically tapering wall;
    a cover element to close said at least one aperture defined by the frontal region, said cover element engages to an inner surface of said frontal region and having a rotational axis perpendicular to said frontal region, said cover element being rotated on said axis.

2. The element as claimed in claim 1, wherein said second conically tapering wall defines a conical angle $\alpha$ which is larger than a conical angle $\beta$ defined by said first conically tapering wall.

3. The element as claimed in claim 1, wherein said second conically tapering wall defines a conical angle $\alpha$ which is in a range 30° to 60° inclusive.

4. The element as claimed in claim 3, wherein said second conically tapering wall defines the conical angle $\alpha$ which is 45°.

5. The element as claimed in claim 1, wherein said frontal region defines a circumference of 180° and includes three apertures which are of substantially equal size and which are uniformly spaced about said circumference defined by said frontal region.

6. The element as claimed in claim 5, wherein each aperture extends over substantially 60° of said circumference defined by said frontal region.

7. The element as claimed in claim 1, wherein said cover element is a substantially disk-shaped member defining a circumference of 180° and includes three openings which are of substantially equal size and are uniformly spaced about the circumference of said cover element.

8. The element as claimed in claim 7, wherein said three openings are separated by a substantially 60° of the circumference of said cover element.

9. The element as claimed in claim 1, wherein said frontal region includes a longitudinal axis of rotation which coincides with said axis of rotation of said cover element.

10. The element as claimed in claim 9, wherein a tubular rivet rotatably attaches said cover element to said frontal region, said rivet including said screw-threaded bore.

11. The element as claimed in claim 1, including means attaching said cover element is attached to said frontal region under a compression force and with no tolerance.

12. The element as claimed in claim 1, wherein said first conically tapering wall includes an inner circumferential surface and includes at least one circumferential groove adapted to engage a correspondingly arranged projection on an outer surface of said socket component.

13. The element as claimed in claim 1, wherein each of said frontal region and said first conically tapering wall and said second conically tapering wall each include an outer surface, and are roughened on at least their outer surfaces with a mean roughness of 5 $\mu$m, according to a Gaussian distribution.

14. The element as claimed in claim 1, wherein said self-tapping screw thread comprises a plurality of teeth, each tooth having a geometric configuration corresponding to a configuration of the corresponding socket component of the artificial hip joint, the configuration including a thickness and height of which substantially correspond to a thickness and height of said socket component for use therewith.

15. The element as claimed in claim 1, wherein said self-tapping screw thread comprises a plurality of teeth, a shape of each tooth being constructed in accordance with the qualities of hardness and porosity of said pelvic bone into which the element is to be fixed.

* * * * *

UNITED STATES PATENT AND TRADEMARK OFFICE
CERTIFICATE OF CORRECTION

PATENT NO. : 5,443,520
DATED : August 22, 1995
INVENTOR(S) : K. Zweymuller

It is certified that error appears in the above-identified patent and that said Letters Patent is hereby corrected as shown below:

Column 7, line 4, Claim 8, After "by" and before "substantially" delete "a"; Column 8, line 13, Claim 14, After "the" and before "configuration" insert ---tooth---.

Signed and Sealed this

Twelfth Day of December, 1995

Attest:

BRUCE LEHMAN

Attesting Officer

Commissioner of Patents and Trademarks